(12) United States Patent
Nekrasov et al.

(10) Patent No.: US 9,155,759 B2
(45) Date of Patent: Oct. 13, 2015

(54) HETEROCHAIN ALIPHATIC POLY-N-OXIDE COPOLYMERS AND VACCINATING AGENTS AND DRUGS BASED THEREON

(75) Inventors: Arkady Vasilievich Nekrasov, Moscow (RU); Natalya Grigoryevna Puchkova, Moscow (RU)

(73) Assignee: OBCHTCHESTVO S OGRANITCHENNOI OTVESTVENNOSTYOU "NPO PETROVAKS FARM", Moskovskaya Obl. (RU)

( * ) Notice: Subject to any disclaimer, the term of this patent is extended or adjusted under 35 U.S.C. 154(b) by 171 days.

(21) Appl. No.: 13/696,857

(22) PCT Filed: Jun. 20, 2011

(86) PCT No.: PCT/RU2011/000429
§ 371 (c)(1),
(2), (4) Date: Nov. 8, 2012

(87) PCT Pub. No.: WO2011/162639
PCT Pub. Date: Dec. 29, 2011

(65) Prior Publication Data
US 2013/0064848 A1    Mar. 14, 2013

(30) Foreign Application Priority Data
Jun. 24, 2010    (RU) .............................. 2010125861

(51) Int. Cl.
| | | |
|---|---|---|
| A61K 31/787 | (2006.01) | |
| A61K 31/424 | (2006.01) | |
| A61K 31/546 | (2006.01) | |
| A61K 45/06 | (2006.01) | |
| C08G 73/06 | (2006.01) | |
| C08L 79/04 | (2006.01) | |

(52) U.S. Cl.
CPC ............ *A61K 31/787* (2013.01); *A61K 31/424* (2013.01); *A61K 31/546* (2013.01); *A61K 45/06* (2013.01); *C08G 73/0627* (2013.01); *C08G 73/0633* (2013.01); *C08L 79/04* (2013.01)

(58) Field of Classification Search
CPC .................................................... A61K 31/787
See application file for complete search history.

(56) References Cited

FOREIGN PATENT DOCUMENTS

| | | |
|---|---|---|
| RU | 2073031 C1 | 2/1997 |
| RU | 2112543 C1 | 6/1998 |
| RU | 2164148 C1 | 3/2001 |
| RU | 2268067 C2 | 1/2006 |
| SU | 523908 A | 1/1977 |

OTHER PUBLICATIONS

Partial English translation of RU 2073031 C1, (c) 1990.
Partial English translation of SU 523908 A, (c) 2005.
English abstract and partial English translation of RU 2164148 C1, (c) 2000.
English abstract and partial English translation of RU 2268067 C2, (c) 2006.
English abstract and partial English translation of RU 2112543 C, (c) 1996.
Plate N.A., "Artificial Kidney", Polymers in Medicine, Moscow, 1968, pp. 38-76 with partial English translation.
Plate N.A., et al., "Physiologically Active Polymers" Moscow, Khimiya, 1986, pp. 3-203 with partial English translation.
Manabu, Senoo, "Polymers for Medical Purposes", Moscow, 1981, pp. 8-25, 144-149, 247.

*Primary Examiner* — Noble Jarrell
*Assistant Examiner* — John S Kenyon
(74) *Attorney, Agent, or Firm* — Ladas & Parry LLP

(57) ABSTRACT

Heterochain aliphatic poly-N-oxide copolymers of general formula (1), where R=N, CH; x=2 or 4; y=0 or 2; n=10-1000; q=(0.1-0.9)n; z=(0.1-0.9)n, exhibit pharmacological activity, including an antioxidant effect and a therapeutic effect as a detoxicant and immunomodulating agent. The copolymer may be used as vaccinating agent also comprising an antigen and a vaccine against hepatitis A and hepatitis B, which contains a vaccine preparation comprising HVA Ag and HBsAg simultaneously or vaccine preparations against hepatitis A and against hepatitis B. The invention represents a new class of compounds that exhibit a wide range of pharmacological activity and a vaccination effect as well as increased safety in use, and is directed towards increasing manufacturability, cost efficiency and environmental safety in the production of drugs.

3 Claims, 1 Drawing Sheet

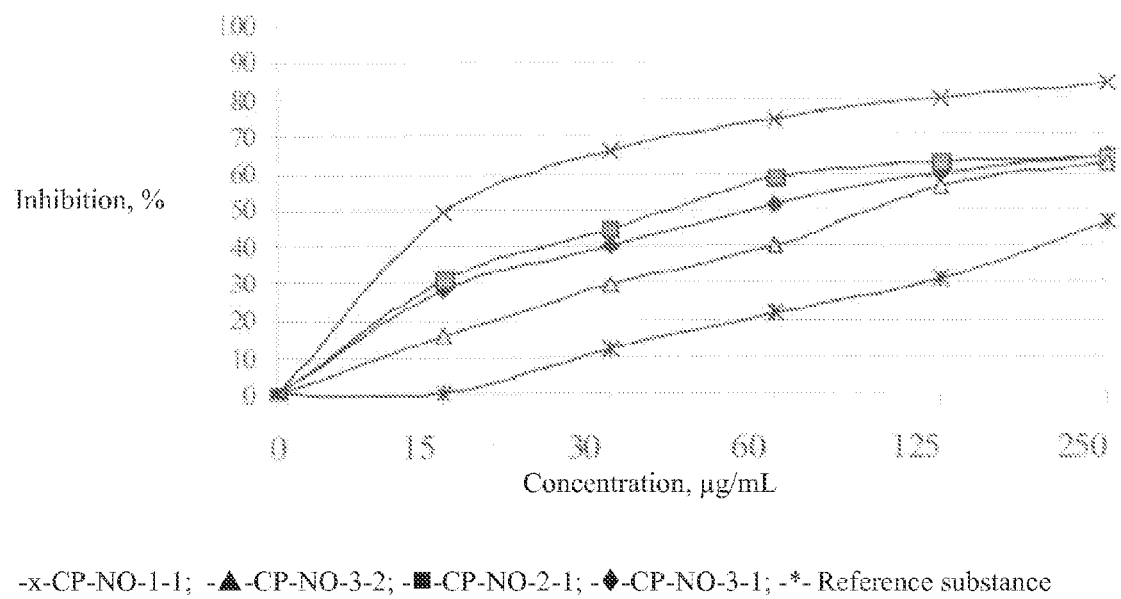
-x-CP-NO-1-1; -▲-CP-NO-3-2; -■-CP-NO-2-1; -♦-CP-NO-3-1; -*- Reference substance

HETEROCHAIN ALIPHATIC POLY-N-OXIDE COPOLYMERS AND VACCINATING AGENTS AND DRUGS BASED THEREON

RELATED APPLICATION INFORMATION

This application is a 371 of International Application PCT/RU2011/000429 filed 20 Jun. 2011 entitled "Heterochain Aliphatic Poly-N-Oxide Copolymers And Vaccinating Agents And Drugs Based Thereon", which was published on 29 Dec. 2011, with International Publication Number WO 2011/162639 A1, and which claims priority from Russian Patent Applications No.: 2010125861 filed 24 Jun. 2010, the contents of which are incorporated herein by reference.

FIELD OF THE INVENTION

The invention relates to the field of synthesizing high molecular weight chemical compounds that exhibit biological activity and can be used for the production of highly effective pharmacological preparations and vaccines.

BACKGROUND OF THE INVENTION

Known are synthetic polymers exhibiting physiological activity, for example, homo and acrylic and crotonic acid copolymers, N-vinylpyrrolidone copolymers with metacrylic and crotonic acids, acrolein, vinyl amine, maleic anhydride and other vinyl monomers (Polymers in Medicine, translated from English and edited by Plate N. A., Moscow, 1969, p. 38-76). Known are also some water-soluble carbonchain polymer derivatives (Plate N. A., Vasiliev A. E. "Physiologically Active Polymers", Moscow, Khimiya, 1986, p. 12-204; "Polymers for Medical Purposes" edited by Senoo Manabu, translated from Japanese, Moscow, 1981, 248 p.) comprising nitrogen in the side chain of a macromolecule such as polyvinyl pyridines and polyvinyl triazoles. All the above mentioned compounds are toxic and are not widely used as pharmacological preparations. Furthermore, carbonchain polymers do not fall in the organism into low molecular compounds, accumulate and cause undesired side effects.

Poly-1,4-ethylene piperazine derivatives are compounds closest in biological effect and chemical essence to the describable invention (RF patent No 2073031, IPC C 08 G 73/02 published in 1997). The known compounds are characterized by a broad spectrum of pharmacological activity and successfully used as carriers of vaccine agents or drugs, as well as in the complex therapy of diseases accompanied with immunodeficiency disorders. At the same time, the presence of ionogenic groups in these compounds reduces the rate of their destruction and elimination from an organism restricting thereby the use thereof for intravenous administration as a detoxicant if rapid elimination of high toxic compounds is required. Moreover, the technology of producing the known compounds supposes a multiple-stage process associated with a high expenditure of expensive chemical agents requiring mighty generating capacities and labor costs.

SUMMARY OF THE INVENTION

The present invention is based on the problem of developing a new class of compounds exhibiting a wide range of pharmacological and vaccinating activity, exhibiting pronounced antioxidant and detoxification properties and safe in use.

Another problem of the present invention is promoting the manufacturability, cost efficiency and environmental safety of the production of drugs.

This problem is solved by new compounds which are heterochain aliphatic poly-N-oxide copolymers of general formula (1):

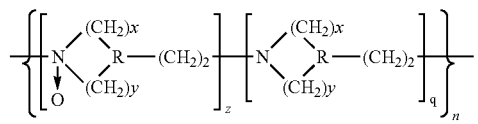

Where: R=N, CH;
x=2 or 4; y=0 or 2; n=10-1000; q=(0.1-0.9)n; z=(0.1-0.9)n exhibiting pharmacological activity.
Wherein:
the copolymer in which x=4, y=0, R=CH has formula (2)

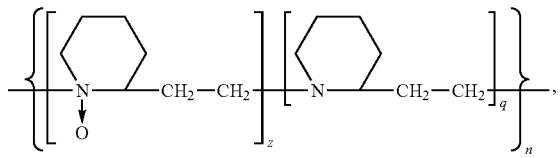

and is a conidine and N-oxide conidine copolymer.
the copolymer in which x=2, y=2, R=CH has formula (3)

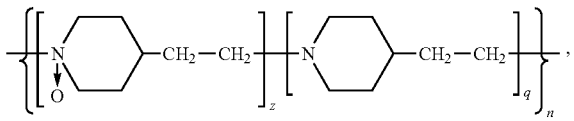

and is a quinuclidine and N-oxide quinuclidine copolymer.
the copolymer in which x=2, y=2, R=N has formula (4)

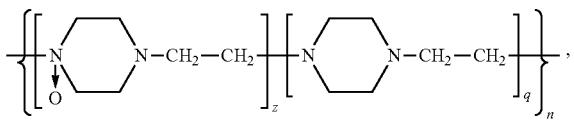

and is a triethylenediamine and N-oxide triethylenediamine copolymer.

BRIEF DESCRIPTION OF FIGURE

FIG. 1 shows the effect of SP-3-NO to the radical reaction by the ability to inhibit the reactive oxygen production.

DETAILED DESCRIPTION OF THE INVENTION

The copolymer of formula (1) can exhibit an antioxidant effect.

The copolymer of formula (1) can exhibit a therapeutic effect and can be a detoxicant.

The copolymer of formula (1) can exhibit a therapeutic effect and can be a immunomodulating agent.

The copolymer of formula (1) can be an immunoadjuvant.

The copolymer of formula (1) can be an immunomodulating carrier for an antigen and a carrier of a medicinal substance.

The problem as set is also solved by that a vaccinating agent comprising an antigen and an immunomodulating carrier contains as an immunomodulating carrier a formula 1 copolymer.

The vaccinating agent, according to the invention, derived in the form of a conjugate of an antigen with heterochain aliphatic poly-N-oxide copolymers of formula (1) is preferred: having in the structure of the antigen reactive functional groups.

The vaccinating agent, according to the invention, derived from a complex-formation reaction of an antigen with a formula 1 copolymer is preferred.

The vaccinating agent, according to the invention, derived from mixing the antigen with a formula 1 copolymer is preferred.

The problem as set is solved by that a vaccine against hepatitis "A" and hepatitis "B" is characterized by that it contains a vaccine preparation comprising simultaneously HVA Ag and HBsAg or vaccine preparations against hepatitis A and against hepatitis B and a formula (1) heterochain aliphatic poly-N-oxide copolymer.

A vaccine against hepatitis A and hepatitis B comprising as HVA Ag antigens derived from strain LBA-86 of hepatitis A virus in a culture of continuous cells 4647 is preferable, and the content of components in a dose is HVA Ag 40-60 EIA units
HBsAg 2.5-20 μg
CP—NO 0.1-10 mg The problem as set is also solved by that a drug comprising a medicinal substance and a carrier contains as a carrier a formula 1 copolymer.

A drug, according to the invention, which is a conjugate of a medicinal substance with a copolymer according to claim 1 is preferred having in the structure of the medicinal substance reactive functional groups.

A drug, according to the invention, which is a compound derived from a complex-formation reaction of a medicinal substance with a formula 1 copolymer is preferred.

A drug, according to the invention, which is a pharmaceutical composition derived from mixing the medicinal substance with a formula 1 copolymer is preferred.

The problem as set is also solved by that a vaccine composition comprising a vaccine preparation and an immunoadjuvant contains as an immunoadjuvant a formula 1 copolymer.

The claimed invention is a new class of compounds exhibiting pharmacological activity, and primarily, exhibiting pronounced antioxidant and detoxification properties, immunomodulating, antiviral and antibacterial activities.

The heterochain aliphatic poly-N-oxide copolymers (CP—NO) are biogenic in accordance with formula 1, inasmuch as they are analogs of natural oxidative metabolism products of natural heterochain polyamines and are applicable for developing drugs safe for a living organism.

CP—NO biodestruct in an organism into oligomeric and low molecular compounds and are completely eliminated from an organism.

Due to own pharmacological activity based on the compounds in accordance with the invention, high efficient ballast-free pharmacological systems can be developed. The presence of free reactive tertiary nitrogen atoms in the claimed compound makes it possible to modify thereof for introducing new reactive group into the side chain of CP—NO followed by using them as carriers for conjugated vaccines, enzymes, different drugs. Preparing CP—NO-based conjugated compounds is possible only when having reactive groups in vaccine antigens, enzymes, drugs.

The claimed invention provides a unique adsorbing capability that is determined by a combination of physicochemical properties of these compounds, namely:

a wide range of molecular weights including high molecular weights;

the presence of a plurality of weakly-charged N-oxide groups in the backbone chain of a macromolecule, and, as a consequence, a property of forming equilibrium electrostatic complexes with other molecules;

high polarity (the dipole moment of N—O-bond is about 5 D exceeding thereby the dipole moment of other bonds almost by an order) allowing the formation of stable electrostatic macromolecular complexes.

forming chelate complexes with metals, and, as a consequence, effective protection of cellular membranes.

Due to these properties, the describable compounds adsorb different toxins, including metals, metabolic products and others, and then eliminate them from an organism. The pronounced detoxification and membrane-protective properties of these compounds are determined by the particularly adsorptive capacity and polymeric nature.

In their detoxification properties, the copolymers in accordance with the invention hundreds of times excel the detoxification properties of the known compounds of the same purpose, such as hemodez, albumin, dextran, and others.

At the same time, the describable copolymers have noticeable immunomodulating properties—the stimulation ratio varies within 3÷7.

The claimed invention allows also developing vaccinating and therapeutic agents of a new generation that, owing to the high molecular immunostimulator—a carrier of antigens and allergens of CP—NO, are characterized by a great stability of antigens, enhancing immunogenicity by decreasing of an inoculation antigen dose, more effective formation of immunological memory to antigens and increasing the prophylactic efficiency of vaccines, as well as a high safety level of vaccines and therapeutic agents.

The claimed invention allows also enhancing the immunogenic activity by modifying antigens of different nature with the high molecular CP—NO immunostimulator.

When attaching CP—NO to allergens, the claimed invention allows also reducing the allergic activity, improving the safety of the preparation and reducing the risk of complications when administering thereof to a sensitized organism. Binding the allergens to CP—NO makes it possible to considerably enhance the immune response, to promote a high level of producing allergen-specific IgG antibodies giving protection to allergic patients when allergen-containing substances are penetrated into an organism thereof.

Other purposes and advantages of the present invention will become clear from the following detailed description of the compounds which are heterochain aliphatic poly-N-oxide copolymers of general formula (1) of the vaccine preparations and drugs based thereon.

EMBODIMENTS OF THE INVENTION

CP—NO in the structure have N-oxide groups. From the chemical point of view N-oxide compounds differ from other compounds in the highest polarity (the dipole moment of N-oxide is about 5D, whereas the dipole moment of the initial polyamide is 0.65D). This determines their unique capability to absorb various toxic compounds, metals and products, and then to eliminate them from an organism. The pronounced detoxification of these compounds is determined particularly by such an adsorptive property.

CP—NO can be used as carriers of other pharmacologically active compounds by covalent binding thereof, wherein the covalent binding is achieved by introducing chemically high reactive groups.

The immunogenic and protective properties of the derived CP—NO conjugates with different antigens, including influenza virus (IV) hemagglutinin were evaluated by studying the responses of the immune system and an organism in general on experimental animals.

It has been detected that administering the conjugate of IV-CP—NO to an animal organism induces a noticeable antibody response by a single administration of the conjugate. In response to the readministration, a secondary, more intensive response develops, reaching the maximum after 10-15 days, it is more longstanding, maintains very high values even in 3 months after immunization. In experiments on animals high immunogenicity of the conjugate in the hemagglutination inhibition test HIT is demonstrated. Direct virus-neutralizing activity of the antibodies being formed has been revealed in blocking test of propagating a live virus in chicken embryos. According to these tests, the conjugate is as good as the whole virion reference vaccine. An analysis of antibody isotopes has found that antibodies IgM, IgA, primarily IgG, but not IgE are formed. The formation of immune memory is initiated saying thereby about involving T-cells in response to administration of the conjugate, T-helpers being accumulated. What is of critical importance, the heavy formation of virus-specific T-killers is induced.

CP—NO derivatives have a broad spectrum of pharmacological activity, high bioavailability, a property of being eliminated from an organism, safety in use.

CP—NO in a wide range of doses activates the macrophage element, humoral immune response, exhibits anti-infectious and antitumor activity, improves the resistance of cell membranes to a cytotoxic effect and reduces the toxicity of drugs when jointly administered.

CP—NO is derived from chemical synthesis by partially oxidizing the tertiary nitrogen of the backbone chain of an initial aliphatic polyamine macromolecule comprising nitrogen in the backbone chain in weakly acid aqueous, aqueous alcohol and alcohol solutions. As an oxidant, hydrogen peroxide and other organic or non-organic peroxides or hydroperoxides, salts of oxygen-containing halogen acids, ozone, or oxygen produced by water electrolysis can be used.

Synthesis is performed at a temperature of 20° C.÷40° C. The solvent and a peroxide surplus are removed by the ultrafiltration method, and then cool dehumidification is done.

Identifying and analyzing the structure of resultant CP—NO and derivatives thereof are carried out by means of the physicochemical analysis methods: NMR-, PMR-, IR-spectroscopy, UV-spectroscopy. Molecular weight characteristics are obtained by using a chromatographic complex comprising a high effective liquid chromatograph having 4 detectors—UV-spectrophotometry, refractometry, low-angle laser light scattering, and fluorescent spectroscopy.

For preparing CP—NO conjugates and complexes with proteins and glycoproteids of different nature having a primary amino group or a carboxyl group, as a protein component of this reaction, there can be used:

- for producing vaccinating preparations—antigenic complexes isolated from the causative agent of hepatitis A, B, C, tuberculosis, anthrax, cholera, typhoid fever, pertussis, diphtheria, tetanus, pyogenic infections;
- for preparing long acting drugs having a high safety and efficiency level—erythropoietins, cytokines, interferons, enzymes, cytostatics, antibiotics, hormones, vitamins;
- for preparing specific immunotherapy agents—allergens and allergoids isolated from plant and grass pollen, domestic dust, foods and others.
- In each specific case reacting conditions vary—the component ratio, pH, reaction temperature, the process duration, the concentration of reagents in a reaction mixture thereby influencing the yield and composition of the preparation obtained.

For using CP—NO as a carrier of different pharmacologically active compounds, methods of complex-formation binding by multi-point electrostatic interactions of components and covalent binding can be used.

If antigens are individual compounds having known chemical composition and structure—Vi-antigen, hemagglutinin, enzymes, etc., it is preferable to choose covalent binding. If this is a mixture of different substances, it is preferable to carry out complex-formation binding including by using polymer-antigen-metal complexes.

In case of oppositely charged compounds the complex formation under definite conditions happens with a high rate and yield. In case of like-charged compounds, methods of preparing to form polymer-antigen-metal complexes are preferable. For example, in a specific case when using timothy or birch pollen as an allergoid, which are not an individual compound. When binding the allergoid to CP—NO, both compounds have a weak negative charge, that is, they are like-charged. In this case, a complex-formation reaction using polymer-metal complexes is chosen.

The basic criteria therein are safety, efficiency and manufacturability of processes of synthesizing compounds and producing pharmacological preparations.

The comparison of different binding methods has discovered the advantages of particularly forming triple polymer-antigen-metal complexes. The manufacturability is exclusively high—against the background of preliminary complex-formation of two compounds an estimated amount of copper salt is added to produce "clips" between molecules determining thereby the resistance of a complex under physiological conditions.

The formation of triple polymer-metal complexes based on CP—NO and ions of transitional metals and antigens or allergens appeared to be one of the optimal methods at which sufficiently strong binding of an antigen and a polymeric carrier is not accompanied with a change in their chemical structure and, as a consequence, the spectrum of biological effect of components, does not result in appearing toxic reaction by-products and has some technological advantages, as the method of preparing triple polymer-metal complexes is easy, manufacturable, moves in one step in soft conditions having a 100% yield.

In the vaccine and pharmaceutical compositions developed, an immunomodulating, anti-infectious and anti-inflammatory effect is determined by a combination of physiological activity of CP—NO with activity of components.

The examples given below illustrate a possibility of deriving copolymers in accordance with the present invention and the results of studying their properties.

In following examples 1-5 there are given examples of synthesizing specific CP—NO; examples 6-13 illustrate studying the pharmacological properties of CP—NO; in examples 14-20 there is given a possibility of preparing conjugates and complexes of CP—NO derivatives with different physiologically active components resulting in formation of vaccine and pharmaceutical compositions on the basis thereon.

Examples 1-3 show variants of synthesis of CP—NO by using three initial heterochain aliphatic polyamines, poly-1, 2-conidine of CP—NO-1, poly-1,4-quinuclidine of CP—NO-2, poly-1,4-triethylenediamine of CP—NO-3, respectively.

Example 1

Synthesis of Conidine and Conidine-N-Oxide Copolymer (CP—NO-1-1)

For synthesis of a copolymer, a heterochain aliphatic polyamines, poly-1,2-conidine, is used.

10 g of initial polyamine with MM 70000D are dissolved in 300 ml of 96% ethyl alcohol. The solution is cooled to a temperature of 4÷6° C. and while simultaneously agitating 20 ml of 30% hydrogen peroxide are added. An oxidation reaction of polyamine is carried out for 10 hours, after which a portion of the solvent is removed in vacuum and 300 ml of water is added. Unreacted hydrogen peroxide is removed by means of an ultrafiltration plant "Pelikon". The resultant solution of conidine and conidine-N-oxide copolymer is concentrated and dried on a cool dehumidifier. After drying the yield of the desired product is 99%, n=620, q=0.35n, z=0.65n.

The Data of an Ultimate Analysis:
Calculated, %: C, 66.3; H, 10.24; N, 11.20;
Received, %; C, 66.4; H, 10.31; N, 11.22;

The characteristic compound band obtained from an analysis by the IR-spectrometry method is 960 $cm^{-1}$ and 1130 $cm^{-1}$.

Example 2

Synthesis of Poly-1,4-quinuclidine and 1,4-quinuclidine

N-oxide copolymer (CP—NO-2-1)

Poly-1,4-quinuclidine with MM 75000D 10 g is dissolved in 150 ml of 0.1 N acetic acid. While cooling (4° C.) and agitating, 10 ml of 30% hydrogen peroxide is added. The solution is held in these conditions for 24 hours. Then the solution is subjected to ultrafiltration to remove an surplus of hydrogen peroxide and acetic acid. An aqueous solution of the copolymer is freeze-dried.

The characteristic compound band obtained from an analysis by the IR-spectrometry method is 960 $cm^{-1}$ and 1130 $cm^{-1}$.

The yield of product is 100%: n=650, q=0.2n, z=0.8n.

Example 3

Synthesis of Poly-1,4-triethylenediamine and Poly-1,4-triethylenediamine N-oxide Copolymer (CP—NO-3-1)

10 g of initial polyamine of poly-1,4-triethylenediamine with MM 80000D are dissolved in 400 ml of acetic acid at pH5. After dissolving polyamine while agitating and cooling (4-6° C.), 20 ml of 30% hydrogen peroxide is added. The reaction is carried out for 35 hours. Upon completion of the reaction the resultant solution is purified from a surplus of unreacted components using the purification method by ultrafiltration, then it is subjected to freeze-drying. After drying, the yield of the desired product with characteristics: n=700, q=0.25n, z=0.75n is 100%.

In table 1 there are given characteristics (m, q, z and MM) of conidine and conidine-N-oxide copolymer (CP—NO-1-1, CP—NO-1-2, CP—NO-1-3), 1,4-quinuclidine and 1,4-quinuclidine N-oxide copolymers (CP—NO-2-1, CP—NO-2-2, CP—NO-2-3), and 1,4-triethylenediamine and triethylenediamine N-oxide copolymers (CP—NO-3-1, CP—NO-3-2, CP—NO-3-3) deriving according to the procedures described in examples 1, 2, 3, respectively with varying ratios of initial components and reaction parameters.

For the purpose of further using as an immunostimulating carrier for preparing conjugates with antigens and medicinal substances having reactive functional groups, synthesis of activated CP—NO derivatives by modification reaction of tertiary nitrogen atom is possible.

Example 4

Study of Pharmacokinetics of Different CP—NO Types Having a Radioactive Label $C^{13}$ The investigation of the pharmacokinetics of labeled CP—NO is performed according to the standard procedures by intramuscular administration of a dosage form with CP—NO in a dose of 20 mg/kg (0.75 MBq/kg) to rats.

Observations of animals showed the absence of tissue accumulation of the preparation. Heterogeneity was detected in the distribution of CP—NO in organs and tissues in males and females. The elimination of CP—NO takes place primarily in two phases. The elimination half-life time of the rapid phase is 1.5 hours, of the slow phase is 84 hours.

The investigation results of pharmacokinetics of CP—NO-1-1, CP—NO-2-1 and CP—NO-3-1 presented in table 2 show that CP—NO quickly absorbs into the systemic circulation and reaches the maximum concentration already after 30-50 min. The distribution half-life is about 0.5 hour, elimination half-life is 20-46 hours, and the average retention time of the preparation in an organism is approximately 40 hours.

Example 5

Study of the Antioxidant Properties of CP—NO

A capability of CP—NO of suppressing the formation of active oxygen forms (AOF) is evaluated in the system of reacting hydrogen peroxide with horseradish peroxidase (Reanal). Herewith, forming superoxide anion-radicals is recorded by chemo luminescence according to the oxidation intensity of luminol by the products of said reaction. An analysis of chemo luminescence is done on a 36-channel plant "Lucifer-B" at a temperature of 37° C.

An interaction medium is preliminarily prepared composed of: a phosphate-buffered physiological solution (pH 7.2÷7.4), luminol (Sigma Chemikal Co. in the final concentration of $0.6 \times 10^{-3}$ M) and reacting reagents—hydrogen peroxide (in the concentration of up to 0.005%) and horseradish peroxidase (in the final concentration of 1 µg/ml).

Said ratio of reagents retains intensive chemiluminescence at the level of 300000 counted per second within 40 minutes. The finished mixture is placed in the volume of 500 µl in test-tubes of a chemoluminograph and luminescence level is recorded for 5 min. Then to a relevant test tube the investigated substances are added (CP—NO-1-1, CP—NO-2-1, CP—NO-3-1, CP—NO-3-2) in the volume of 10 µl. The range of the concentration being investigated is from 25 to 250 µg/ml. Under such a procedure, there was dose-dependent signal blanking by 10÷90% of the reference level. The measurements are ceased upon moving a chemo luminescence curve on the Plato (after 15÷20 min). For each concentration of the substance introduced the area under curve was calculated and compared it with the same for control test tubes with a normal saline solution.

The results are expressed in percents of suppressing a free-radical reaction for each concentration of the substances investigated. To compare the anti-radical activity of different samples, the concentration is calculated at which the suppression of activity of 50% of free radicals takes place.

The data given on diagrams of FIG. 1 testify that adding to the radical reaction system of all investigated CP—NO samples in the concentration of 15 μg/ml results in suppressing the a radical reaction level to much more degree (by 50%) compared to the known compound (reference preparation) in the same dose (by 30%) which confirms high antioxidant properties of the describable compound.

Example 6

Study of the Detoxificaton Properties of CP—NO

The protective properties of CP—NO are evaluated on an acute toxicity model.

In the investigations white mice—hybrids weighing 18-20 g are used (model CBAxC57BL/6F1) are used.

0.04% solutions of the naturally occurring substance toxic for mice are prepared—MRM added and no CP—NO in a ratio of 1:1 and 1:5 used in the experimental investigations. The investigated compounds are administered once to animals intraperitoneally in the volume of 0.25 and 0.5 ml, according to the doses. The normal saline solution in an amount 0.5 ml is administered to the animals of the control group. Observations of animals are performed for 21 days.

The data presented in table 3 illustrate the protective properties of CP—NO.

Example 7

Study of the Antidotal Properties of CP—NO

The investigation was done in vivo at an acute $CuSo_4$ poisoning. The preparations are administered to 7 groups of animals of which a normal saline solution is administered to the animals of the first group, $CuSo_4$ alone in the doses fatal for animals (mg/kg): 12.5; 25.0; and 50.0 to the animals of groups 2÷4, and the similar $CuSo_4$ doses in combination with the similar doses of CP—NO-3-1 are administered to the animals of groups 5÷7.

The results of investigations presented in table 4 testify to a pronounced antidotal effect of CP—NO.

Besides, it has been found that simultaneously administering CP—NO-3-1 in a dose of 12.5 mg/kg and more with three fatal $CuSo_4$ doses not only protects animals from death but also prevents developing intoxication symptoms.

Example 8

Evaluation of the Protective Properties of CP—NO on an Erythrocyte Hemolysis Model The investigation was done on a model of quartz ($SiO_2$) erythrocyte hemolysis using the international standard of quartz dust DQ-12 having a dispersion degree of less than 3 μm according to the A. David method (1976). Human blood was taken with heparin, erythrocytes were thrice washed in a 10-fold volume of a water-white Henx solution followed by centrifuging at 3000 rpm for 10 min. An erythrocyte suspension was resuspended to a 4% concentration ($10^6$ erythrocytes in 1 ml). All investigations were done in 3÷5 parallel assays.

The samples of $SiO_2$ and erythrocytes were taken under continuous agitation on a magnetic agitator.

1 ml of a 4% erythrocyte suspension was mixed with 1 ml of the investigated preparation adding 1 ml of 0.3% (3 mg/ml) of a $SiO_2$ suspension and incubated for 1 hour at a temperature of 37° C. carefully shaking the samples every 5 minutes. After incubation all samples were added with 7 ml of a buffer, it was centrifuged and the supernatant was photometered on SF-26 at 540 nm. The results of hemolysis were expressed in percents taking as 100% the content of hemoglobin in the samples of 1 ml of a 4% erythrocyte suspension with 9 ml of distilled water. The protective effect of the investigated preparations was calculated according to the formula and expressed in percents:

$$100 \frac{E_{540} \text{ test}}{E_{540} K \text{ sio}_2} \times 100,$$

where:

$E_{540}$ K $SiO_2$ is extinction of the control samples—a "water-silicon-erythrocytes" test tube.

The data given in table 5 show that silicon dioxide exhibit pronounced hemolytic properties. 3 mg of $SiO_2$ for an hour of incubation induces hemolysis of 87.4% erythrocytes. The incubation of erythrocytes with $SiO_2$ in the presence of 50 μg of CP—NO-3-2 actually entirely protects erythrocytes from hemolysis.

A property of CP—NO to protect erythrocytes from hemolysis was compared to high molecular plasma-substituting solutions of polyvinylpyrrolidone (hemodez), dextran (polyglucin) and albumin. As a buffer, a water-white Henx solution was used.

Polyvinylpyrrolidone and albumin also exhibit protective properties, but a pronounced effect is achieved only in high doses. The preparation does not destruct therewith, it may accumulate in an organism and induce undesired side effects.

The data presented in table 5 convincingly testify to pronounced properties of CP—NO as a detoxicant and to their advantages compared to the recognized detoxicants.

Example 9

Study of Imminomodulating Activity of CP—NO

The imminomodulating activity of CP—NO was evaluated by their capability of promoting the antibody formation to sheep erythrocytes or protein antigens (B-subunit of cholera toxin, tetanus toxoid) in the experimental first generation hybrid mice produced by crossing mice of CBA and C57BL lines (model CBAxC57BL/6F1) by determining the number of antibody-producing cells (APC) in mouse spleen in 4-7 days after their combined administration. Experimentation according to the common Erne method. The number of APC in mouse spleen is determined by the method of local hemolysis in agar. The antibody titers formed in response to administering protein antigens are determined by the enzyme immunoassay. The immunomodulating activity of CP—NO is evaluated towards the APC number formed by combined administering antigens and CP—NO towards the AFC number in the control group animals. The dose varies from 1 to 1000 mg/kg per mouse for intraperitoneal and subcutaneous administration.

In table 6 there are given values of the stimulation index depending on a specific compound and an administration dose (the dose varied from 1 to 1000 mg/kg per mouse for intraperitoneal and subcutaneous administration). The stimulation index of immune response is a value of 3 to 7, that is, is comparable with the known standard toxic stimulant—polyacrylic acid (PAA). The experiments showed that there was a dependence of the stimulation ratio value on the dose and composition of CP—NO.

The investigation results testify to a high immunomodulating activity of CP—NO exhibiting in a wide range of doses at different techniques of administration.

Example 10

Preparing an Anti-Tuberculosis Vaccine by Complex Formation of an Antigenic Complex Isolated from a Triton Extract of BCG Mycobacteria with CP—NO. Evaluation of the Preparation Protective Properties in an Experiment on Animals Some samples of an anti-tuberculosis vaccinating preparation having an optimized ratio of an antigen and CP—NO-3-1 have been prepared and studied.

As an antigen, an antigenic complex (AC) consisting of glycopeptides isolated from a triton extract of cell walls of BCG mycobacteria was chosen.

According to the antigen specifications data, the content of protein in 1 mg of AC dry matter is 50.2 µg. Protein is determined according to the Bradford method.

Preparing samples of the vaccinating preparation proceeded from the approximate dose for antigen—100 µg and 50 µg of AC per mouse, a dose for protein was 5 µg and 2.5 µg per mouse, respectively. A dose of CP—NO-3-1 was chosen on the basis of earlier results and was 1000 µg per mouse. To produce vaccinating preparations, a CP—NO-3-1 compound was used. When determining the ratio of components composed by the preparation, the content of the basic substance of CP—NO-3-1 was estimated.

A complex-formation reaction is carried out as follows.

500 mg of CP—NO-3-1 is dissolved in 10 ml of 0.05 phosphate buffer pH=5.8. At a temperature of 2-4° C. 100 mg of an AC solution in 2 ml of the same buffer is added. At this pH value, polymer carrier macromolecule and antigens are oppositely charged.

A complex-formation reaction is carried out by slowly introducing an antigen solution into a CP—NO-3-1 solution preventing from precipitation. Increasing the solubility of the antigen complex in water is implemented by its complex formation with CP—NO. In one of the variants (Preparation 1) a solution of pharmaceutical CP—NO composition is added to the antigen complex by continuously agitating and controlling the pH. In the other variant (Preparation 2) the antigen and CP—NO solutions are combined by continuously agitating, cooling and controlling the pH.

After synthesis, the preparation solutions are subjected to freeze drying and control.

Determination of the protein content and an analysis are carried out by methods of fluorescent spectroscopy and polyacrylamide gel electrophoresis (PAGE). The characteristics of the two preparations produced by the describable techniques are given in table 7.

The protective activity of synthesized preparations 1 and 2 is evaluated according to two indicators—according to the isolation rate of mycobacteria from lungs and spleen of inoculated mice, as well as according to the post infection survival terms.

The immunization of mice involved 3 preparations:
Preparation 1 contains 5 µg of antigen and 500 µg of CP—NO per dose;

Preparation 2 contains 2.5 µg of antigen and 500 µg of CP—NO per dose;

Preparation 3 contains 500 µg of CP—NO per dose.

The mice are immunized with preparations 1, 2, 3 subcutaneously in 1 point in the volume of 0.2 ml twice 2 weeks apart. As a positive control, the animals received 1 BCG injection (Prague $10^6$) are used. Unvaccinated animals are used as a negative control.

In 5 weeks after the second immunization, experimental animals of each group are inoculated with the lethal dose of Mycobacterium tuberculosis H37Rv ($5 \times 10^6$ CFU).

The isolation rate of mycobacteria from organs is determined 3 weeks after administration of the lethal mycobacteria dose. From the results given in table 8 there is observed a reduction in the CFU number in lungs and spleen of mice vaccinated with the preparations compared to the CFU number in control group 4 of animals received an injection of the lethal mycobacteria dose.

As to the survivability of the experimental animals, Preparation 2 seems to be most efficient. This preparation has a protective effect from the lethal mycobacteria dose in 57% of animals by observation day 70, however, the preparation was somewhat less efficient than BCG. The double administration to animals of preparations 1 and 2 extends the lifetime of lethally inoculated mice by 16 days.

The data presented in table 9 show the efficiency of the prepared vaccines as to the survivability.

Thus, from the received data, the preparation in which the protein content (within AC) and CP—NO is 5 μg and 500 μg, respectively, had the greatest protective effect. Its effect was truly higher than in the case of the other preparations used.

Example 11

Preparing Conjugates of CP—NO with Proteins and Glycoproteides of Different Nature Having a Primary Amino Group in the Side Chain For preparing conjugates and complexes of CP—NO with proteins and glycoproteides of different nature having a primary amino group or c carboxyl group, as a protein component, in this reaction there can be used:

- for producing vaccinating preparations—antigenic complexes isolated from the causative agent of hepatitis A, B, V, tuberculosis, anthrax, cholera, typhoid fever, pertussis, diphtheria, tetanus, pyogenic infections;
- for preparing long acting drugs having a higher safety and efficiency level—erythropoietins, cytokines, interferons, enzymes, cytostatics, antibiotics, hormones, vitamins;
- for preparing specific immunotherapy agents—allergens and allergoids isolated from plant and grass pollen, domestic dust, foods and others.

In each specific case reacting conditions vary—the component ratio, pH, reaction temperature, the process duration, the concentration of reagents in a reaction mixture thereby influencing the yield and composition of the preparation produced.

The method of preparing conjugates of CP—NO with proteins as general has the following sequence of actions: 10 mg of CP—NO prepared according to the above described examples are dissolved in 1 ml of water. The solution is added with 5 mg of bromoacetyl hydrazide, and the mixture is agitated for 23 hours at a temperature of 30° C. Then a solution of 3 mg protein in 0.01 M phosphate buffer pH 8.2 is added to the reaction mixture. A conjugation reaction is carried out at a temperature of 2-4° C. for 20 hours. Upon completion of the reaction the reaction mixture is purified by ultrafiltration method, the desired product is isolated by freeze-drying.

Example 12

Preparing Conjugates of CP—NO with Antigens of Polysaccharide Nature (PS-AG) in Order to Produce Vaccinating Compounds Having a Higher Immunogenicity and a Protective Effect Against Infections Preparing conjugates of CP—NO with antigens of polysaccharide nature (PS-AG) is shown by the example of capsule Vi-polysaccharide exhibiting protective activity against infection induced by *Salmonella typhi*.

The conjugates of PS-AG with CP—NO are prepared using the method described in example 11 by forming a covalent bond between the carboxyl group of N,O-acetylgalacturonic acid residues of PS-AG and a hydrazide group of activated CP—NO derivatives using the condensing agent 1-ethyl-3-(3-dimethylaminopropyl) carbodiimide (EDC). A condensation reaction of PS-AG with a hydrazide CP—NO polyxidonium derivative is carried out in aqueous saline solutions (0.2-0.35 M NaCl) with a weight ratio between the components being equal to 1:0.25-1:10 taken in the concentration of 0.1-0.3% for PS-AG and 0.07-1% for CP—NO for 3-20 hours at a temperature of 4-20° C. and pH 5.6-5.8; the amount of EDC was 0.2-0.5% by weight.

The procedure of isolating a conjugate from the reaction mixture is carried out on a column (2.6×70 cm) having a carrier Sephacryl S-1000 (Parmacia, Sweden) in a 0.2 M NaCl solution. The conjugate fractions going out with a free column value are combined, concentrated in vacuum to a small volume, dialyzed against a normal saline solution comprising 0.01% thimerosal as a preservative and stored at 3-8° C.

The yield of conjugates calculated according to PS-AG is 60=10% of the initial weight PS-AG quantity.

The treatment of the conjugate solution with a 0.5 M NaCl solution or a 0.25% solution of sodium deoxycholate detergent does not result in reducing the molecular weight of the obtainable product according to the data of gel-chromatography on Sephacryl S-1000 and Sepharose 4B testifying thereby to the existence of a covalent bond between PS-AG and CP—NO.

The presence of PS-AG in the prepared conjugates is confirmed by a serological test. The conjugates inhibit the passive hemagglutination test with monoreceptor antiserum in the concentration of 0.12-250 µg/ml. The PS-AG conjugates with a single intraperitoneal immunization of laboratory animals (mice of F1 line) in the dose of 5-100 µg/mouse produce specific serum antibodies in an amount of 2-4 times more than the initial PS-AG.

The example of preparing sample No.1—conjugated Vi-polysaccharide (Vi-PS) having a molecular weight of 3-5 MD, which is a linear homopolymer consisting of 3-O-acetyl-2-acetamido-2-deoxyD-galacturonic acid residues linked by (1-4)-glycosidic bonds with a hydrazide CP—NO derivative synthesized according to the method of example 5. Preparing a conjugated capsule Vi-polysaccharide having a weight V—PS:CP—NO ratio of 1:0.25.

To 10 mg of Vi-PS in 1.7 ml of a 0.2M NaCl solution at pH 5.6 by agitating 2.5 mg of CP—NO in 1.7 ml of a 0.2 M NaCl solution at pH 5.6 are added. The resultant solution is agitated for 30 minutes at 20° C. adding 8 mg of dry EDC. The pH of the solution of 5.6-5.8 is maintained with a 0.1 n HCl solution for 3 hours at 20° C. and 17 hours at 4° C.

The reaction mixture is dialyzed for a day in dialysis tubes (6000-8000, Spectra/Por, US) against a 0.2 M NaCl solution. The dialyzate is applied to the column having a carrier Sephacryl S-1000 (2.6×70 cm). Elution is carried out with a 0.2 M NaCl solution at the rate of 60 ml/h. Registration is implemented by spectrophotometry at 206 nm and refractometry.

The fractions corresponding to the free column volume, k=0.1-0.36, are combined, evaporated to a small volume on a rotary film evaporator, dialyzed against a normal saline solution comprising 0.01% thimerosal pH 7.0 and stored at 3-8° C. The yield of conjugate according to PS-AG is 70%, the weight ratio between the components V—PS:CP—NO in the conjugate is 1:0.3.

The example of preparing sample No.2—conjugated with a hydrazine SP-NO derivative synthesized according to example 6 of capsule Vi-polysaccharide having a weight V—PS:CP—NO ratio of 1:0.5.

As distinct from preparing sample No.1, 10 mg of V—PS in 3 ml of a 0.2 M NaCl solution by agitating and pH 5.6 are added with 5 mg of CP—NO in 3 ml of a 0.2 M NaCl solution at pH 5.6. Dry EDC is added in an amount of 12 mg.

The yield of conjugate according to Vi-PS is 70%, the weight ratio between the components V—PS:CP—NO in the conjugate is 1:0.3.

Example 13

Study of Protective Properties of Conjugates of CP—NO with PS-AG as Vaccinating Compounds Exhibiting High Immunogenicity and Protective Effect Against Infections Induced by Causative Agents *Salmomella*

Investigation was done on vaccine samples No.1 and No.2 prepared in accordance with the technology described in example 15 compared to the native Vi-polysaccharide (Vi-PS).

The preparations are tested on laboratory animals—CBAxC57BL/6F1 mice in tests of active protection of mice from animal infection with the typhoid fever master control virulent strain *Salmonella typhi* Sp. 2 No.4446. An active mouse protection test is the main method of laboratory evaluating the efficiency of typhoid fever vaccines. The requirement for the vaccine preparation studied in this investigation in this test is protection of mice under inoculation with a culture in the dose of 3-6 LD50. Vi-PS and its imunnochemically active conjugates with CP—NO, samples No.1 and No.2, are only once administered. Intraperitoneal administration and inoculation are used, as particularly such a method of administering places the most severe requirements for vaccine immunogenicity. Inoculation is carried out after a month and more after an experimental vaccine administering.

Comparison of the protective properties of conjugate series samples No.1 and No.2 and a commercial typhoid fever vaccine has been conducted. The typhoid fever chemical absorbed liquid is administered. Preparations are injected at a dose equal to that for Vi-antigen.

The comparison of preparations protective properties is also performed using the model of animals inoculation with the virulent strain. Typhoid fever vaccine recommended for comprehensive immunization in the RF is used. The preparations are administered at the dose equal to that of Vi-antigen.

The data on survivability of animals presented in table 10 for samples No.1 and No.2 and their comparison with the commercial vaccine show that conjugation of Vi-PS antigen with CP—NO allows essentially increasing its vaccinating properties and providing a 100% protection of the experimental animals under inoculation of a strain dose not lower than 3 LD50.

Binding PS-AG with a synthetic polymeric immunomodulator CP—NO allows producing a preparation having high immunogenicity.

Example 14

Pyrogenicity Study for Series of Sample No.1 and the Commercial Vaccine

Experiments are performed on 9 chinchilla rabbits to which sample No.1 in the dose of 1000 μg and 200 μg and the commercial vaccine in the dose of 40 μg are administered.

The thermometry results presented in table 11 testify to that the pyrogenic dose (1000 μg) of Vi-PS vaccine with CP—NO considerably exceeds the pyrogenic dose of the commercial typhoid fever vaccine (40 μg).

The investigation results given in examples 16-18 show that the conjugates of polysaccharide Vi-antigen and CP—NO in using against typhoid fever allow considerably improving the protective immunity simultaneously providing a reduction in the preparation pyrogenicity.

Binding PS-AG with a synthetic polymeric CP—NO immunomodulator allows producing an immunochemically active preparation having high immunogenicity, low pyrogenicity and it can be recommended for developing a vaccine preparation against typhoid fever infection.

Example 15

Use of CP—NO to Prepare a Conjugate with a Medicinal Substance

It is shown by the example of preparing a CP—NO conjugate with lidasa (hyaluronidase enzyme)

Preparing a CP—NO conjugate having a drug can be implemented, for example, according to a condensation reaction:

100 mg of CP—NO hydrazide are dissolved in 4 ml of 1 n HCl. The solution is cooled to 2-5° C. Then while agitating and cooling, 1.15 ml of a 3% sodium nitrate solution is added. After 15 minutes the solution pH is made up to 8.5 by adding 2 N NaOH.

A solution of 20 mg of enzyme in 10 ml of 0.05 M phosphate buffer pH 8.5 is added to a CP—NO hydrazide solution. The pH of the reaction mixture is maintained to be 8.5 by adding 2 N NaOH. A reaction is carried out for 12 hours by agitating and cooling (0-2° C.). To isolate and purify the conjugate, the reaction mixture is applied to a column (2.6×90 cm) filled with biogel P-100, as an eluent, phosphate buffer 0.05 M pH 7.5 comprising 0.05M NaCl is used.

The yield of conjugate is controlled by means of a flow spectrophotometer at 226 nm. Determination of the protein content and conjugate analysis is carried out by fluorescent spectroscopy and PAG electrophoresis methods. 1 mg of the preparation comprises 0.2 mg of enzyme.

Example 16

Study of the Antifibrous Properties of the Preparation Based on CP—NO of Conjugate and Lidasa (Preparation L) Produced According to Example 15

The study is performed on Wistar male rats initially weighing 180-200 g on a pneumofibrosis model induced by a single intratracheal administration of 20 mg of quartz dust. The efficiency of Preparation L was evaluated by the content of main components of connective tissue that adequately reflect the degree of fibrosis. In lungs the content of lipids, collagen proteins, glycoproteins, glucose amino glycans was determined, the histomorphological changes and ultrastructure of lungs were also studied.

Preparation L was administered to one group of animals 4 days after dusting. (prophylactic application). To another group—after 1 month, that is, against the background of a developed fibrous process in lungs. Preparation L was administered intraperitoneally in the dose of 1500 IU once a week within 1 month. The third group of animals received native hyaluronidase totally exhibiting the same activity.

The animals were slaughtered after 1, 2 and 3 months. Native hyaluronidase has been found not to have influence on the fibrous process in lungs. At the same time, Preparation L not only hinders the development of the fibrous process, but also exhibits a pronounced capability of resolving the fibrous tissue present in lungs.

Experimental investigations on a pneumoconiosis (silicosis) model have shown a possibility of an efficient impact on the fibrous process by means of Preparation L. The optimum pharmacological dose and dosage schedule of Preparation L has been found at which the preparation not only hinders further development of pneumofibrosis, but also induces regression of granulomas in lungs, which is confirmed by biochemical, histological and electron microscopic studies. The best results of connective tissue growth inhibition for fibrosis destruction for rats can be achieved by administering Preparation L once a week in the dose of 500 IU/kg being equal to 7 CU/kg calculated as Lidasa activity. Lidasa in the same dose and dosage schedule had no noticeable positive effect on the course of fibrosis in lungs.

Physicochemical, and, as a consequence, pharmacological properties typical for the carrier CP—NO play a critical role in realizing the therapeutic effect of Preparation L. The regression of fibrous tissue under influence of Preparation L testifies to that the preparation exhibits a capability of not only inducing connective tissue destruction, but also hindering for the destruction products and silicon dioxide particles having become free from silicotic nodules of promoting again the fibrous process.

The describable example illustrates a possibility of developing drugs having new therapeutic properties by conjugating CP—NO with the known medicinal substance.

Example 17

Use of CP—NO as an Immuno Stimulating Component for Producing Preparations for Specific Immunotherapy Specific immunotherapy or desensitization is a principal etiologic method for treating patients having allergic diseases.

This method giving good stable results in 70-80% of patients is not free from some disadvantages that restrict a possibility of its application. They include: 1) a danger of emerging allergic reactions during a course of immunotherapy both local, and systemic ones; 2) insufficiently high immunogenic activity of small doses of specific allergic preparations to initiate biosynthesis of blocking IgG-Ab. Therefore, one of the main problems of allergology is developing methods of modifying allergic preparations in order to reduce their allergic activity and increasing immunogenicity.

One of techniques of modifying an allergen is binding allergenic and allergoid preparations to high molecular immunostimulators capable of enhancing their immunogenicity, promoting a high level of producing allergen-specific IgG-antibodies and decreasing a possibility of complications by desensitizing therapy.

The modified CO-NO derivatives exhibit reactivity allowing covalently or wholistically binding molecules of different nature having any functional groups.

Choosing the binding tactics depends on the nature of antigenic component. If antigens are individual compounds with the known chemical construction and structure—Vi-antigen, hemagglutinin, enzymes, etc., covalent binding is possible. If this is a mixture of different substances, it is complex formation in case of oppositely charged compounds and triple polymer-antigen-metal complexes in case of like-charged molecules.

A possibility of producing allergovaccines, antigenic component in which is a mixture of different substances is shown by the example of preparing prototype samples of allergovaccines based on allergoid of timothy or birch pollen and CP—NO.

To prepare allergovaccine prototypes based on allergoid of timothy or birch pollen and CP—NO a method of forming triple polymer-metal complexes was chosen.

The safety is provided by the presence of only 5 copper ions per 600 weakly charged N-oxide groups. The manufacturability is exclusively high—at the background of preliminary complex formation of two compounds an estimated amount of copper salt is added to form "clips" between molecules determining thereby the stability of a complex under physiological conditions.

Example 18

Preparing Allergovaccines Based on Allergoid (Ald) of Timothy or Birch Pollen and CP—NO (By the Example of CPNO-3-1)

5 mg of CPNO is dissolved in 10 ml of 0.1N phosphate buffer pH 7.2 adding 5.0 µg of CuSo4.

Then by strongly agitating 5.0 µg allergoid of timothy (or birch) pollen dissolved in 5 ml of phosphate buffer is added. The mixture is held for 8 hours at a temperature of 4+−2° C. The solution is freeze-dried. In the resultant preparation a ratio of Ald:CP—NO is 1:100.

When changing the ratios of components in the reaction mixture, preparations having different amount of protein and different ratio of allergoid and CP—NO within the preparations are produced. To evaluate the allergic activity, three samples prepared according to the described procedure comprising allergoid (for determining protein by the Kieldal method) within conjugates were taken:

in sample 1 Ald: CP—NO—1:100, protein 10 µg/mg of preparation;
in sample 2 Ald: CP—NO—1:20, protein 50 µg/mg of preparation;
in sample 3 Ald: CP—NO—1:10, protein 41 µg/mg of preparation.

Example 19

Evaluation of Allergic Activity of Combined Preparations In Vivo. Determination of Immunogenic Activity of Different Forms of Allergic Preparations Evaluation of allergic activity of combined preparations in vivo was done by using active cutaneous anaphylaxis (ACA) and passive cutaneous anaphylaxis (PCA) in sensitized guinea pigs, as well as by studying a capability of conjugated preparation forms of initiating the formation of IgE-Ab in mice. Said methods allow adequately evaluating the allergic properties of the preparations.

An inhibition test during an enzyme immunoassay (EIA) has shown that conjugated preparations reduce the allergic activity of the native preparation by 60%.

Studying the allergic activity of the native allergen, allergoid and samples No.1, No.2, No.3 in an ACA reaction of sensitized guinea pigs.

Sensitization of guinea pigs with a birch allergen developed stable hypersensitivity of both immediate and delayed types.

The intensity of allergic responses to a specific allergen does not actually vary starting since 3 weeks after the onset of sensitization throughout the successive three months.

Sensitization is expressed in the existence of positive ACA reactions whose intensity depends on an amount of administered intradermal native allergen. The dose dependence of intensity of ACA reaction is traced both by recording the diameter of stained spots in the site of administering the allergen, and by determining an amount of extracted stain.

At the dose of an administered allergen of 5 µg, an ACA reaction developed only in individual animals. On the other hand, increasing the amount of intradermally administered allergen above 100 µg induced staining not only skin, but also substructures making thereby the evaluation of the reaction difficult. Building on that, in the maim number of experiments doses of allergen of 5-100 µg are used.

When administering the allergoid and sample No.2 in such doses, reaction was much weaker that to the respective doses of the native allergen, samples No.1 and No.3. The ACA intensity determined by the amount of the stain appeared in the site of allergic reaction, when administering the allergoid and sample No.2 it reduced compared to the native control, samples No.1 and No.3, when using 100 µg of allergen by 25%, when administering 50 µg—by 30% and when administering 25 µg—by 10%. When administering 12.5 µg, in most animals an immediate allergic reaction did not develop.

Allergic activity of combined preparations in a PCA reaction

Sensitization of mice with allergen, allergoid and vaccinating preparations of samples No.1, No.2 and No.3 induces the formation in them of IgG-Ab which are determined by carrying out a PSA reaction on rats in dilutions of 2/2-1/32 when administering the challenging dose of the native allergen with Evans blue.

The maximum titer of the serum prepared by sensitizing mice with the native allergen and sample No.1 was 1/16. In the variants with allergoid and samples No.2 and No.3 the obtained serum titer was much lower. Thus, by means of ACA and PCA reactions it is shown that conjugated Ald with CP—NO in a ratio of 1:20 and 1:10 reduces the formation of IgG-AT in blood of sensitized animals.

The influence of immunization with a birch allergen, allergoid and combined preparations of Ald with CP—NO on the formation of IgG-Ab As a result of mouse immunization with the native allergen, allergoid and vaccinating preparations of samples No.1, No.2 and No.3 in 3, 5, 6, 7 weeks after the onset of immunization, in animal blood IgG-Ab in titers of ⅛-1/32 were determined.

The level of IgG-Ab in immunized mice in all variants of the experiment changed as time passed. So the serum titer by day 21 in the variants with allergoid, allergen, samples No.1 was 1/32, when immunized with samples No.2 and No.3, it reached the maximum value only on day 42 after the onset of immunization and remained at the sufficiently high level till day 49. The serum titer in which the level of IgG-Ab was determined in the allergoid variant reduced right up to day 42 and increased a little by day 49 from the onset of immunization.

From the data obtained it is apparent that allergens in the form of complexes with CP—NO induce a more intensive immune response.

The conjugation efficiency of Ald with CP—NO has been studied by the method of specific desensitization of sensitized guinea pigs.

After completion of the course of specific hypersensitization the intensity of ACA was the greatest in the control animals, it is taken as 100%.

Hypersensitization with the native allergen and sample No.1 reduced the intensity of ACA compared to the control, when administering 200 µg of allergen by 35% and when administering 25 µg of allergen by 50%. Hypersensitization with sample No.2 was much more efficient. Compared to the control, the intensity of ACA reduces in this case when administering 200 µg of allergen by 65%, and when administering 25 µg of allergen, actually, by 100%.

The reaction intensity for allergoid reduced when administering 200 µg of a birch allergen by 50%.

The similar results are obtained by hypersensitization of guinea pigs by different allergen forms in PCA reactions.

The maximum serum titer 1/32 was achieved in all variants of investigations. However, the amount of stain appeared out of animal skins, corresponding thereby to the reaction intensity, in the experiments with sample No.1 was observed (50%) compared to a reaction in the animals to which sample No.2 and allergoid were administered.

By means of EIA in blood serum of desensitized guinea pigs the level of allergen-specific IgG-Ab is estimated with different forms of birch pollen allergens.

The investigation results show that the IgG-Ab titers in the animals desensitized with allergoid and sample No.1 are 1/8, which is higher than the control, whereas for desensitization with sample No.2, the IgG-AT titer is 1/6. Thus, from all investigated preparations sample No.2 in the injection of 5.0 µg exhibits the highest immunogenic activity.

As a result, the investigations performed have proved:
1. Complex formation of allergen reduces the risk of anaphylactic type reactions.
2. The administration of allergens in combination with CP—NO to an animal organism is not accompanied by increasing IgE-antibodies level in blood.
3. Allergens in combination with CP—NO when administered to an animal organism promote increasing IgG-antibodies level.
4. Preparations of allergen, allergoid and Ald: CP—NO in the test doses (250 µg of protein/kg of animal weight) are non-toxic.
5. A complex allergoid-CP—NO (sample No.1) exhibits (compared to other preparations) more pronounced (by a factor of 1.5-2) desensitizing activity.
6. Complex formation of allergens can be regarded as a general methodical principle allowing achieving the reduction of anaphylactic risk when allergens are administered administration to an organism.

In Example 20 preparation of vaccine compositions based on CP—NO as substances exhibiting an immunoadjuvant effect is described. The use of compounds CP—NO-1-1, CP—NO-2-1, CP—NO-3-1 patented for preparing vaccine compositions is caused by their pronounced immunoadjuvant properties.

Example 20

Preparing Vaccine Compositions by the Example of a Combined Adjuvant Divaccine Against Hepatitis A and B The combined hepatitis di(A+B)-vaccine using the CP—NO compounds being patented may be intended for prophylactic vaccination of different population groups against viral hepatitis. The application of the combined vaccine with a lowered antigenic load will allow reducing the recording frequency of general and local reactions, as well as will considerably reducing the cost of vaccine prophylaxis against hepatitis A and hepatitis B. In this case, promising is the use of combined adjuvant vaccines with a lowered antigenic load for persons having low immunity indicators, as well for persons living in environmentally neglected regions.

Industrial Applicability

The invention heterochain aliphatic amine copolymers and heterochain aliphatic N-oxide copolymers, while exhibiting a great degree of polarity and adsorption property, capable of destructing into low molecular fractions and easily eliminating from an organism will find use as antioxidants, detoxicants and immunomodulating agents, as well as immunoadjuvants and immunomodulating antigen carriers in the production of vaccinating agents and drugs that are characterized by pronounced high bioavailability, capability of eliminating from an organism, safety in use.

TABLE 1

| Sample | Solvent | Concentration of init. PA | Amount of H2O2 30% | Temperature (° C.) | Duration | MM Init. PA | q require. free | z oxyd. | n | MM final product |
|---|---|---|---|---|---|---|---|---|---|---|
| CPNO-1-1 | 96% ethyl alcohol | 10 g in 300 ml | 20 ml | 4-6 | 10 h | 70000 D | 0.35 | 0.65 | 620 | 75000 D |
| CPNO-1-2 | 96% ethyl alcohol | 10 g in 500 ml | 3 ml | 4 | 3 h | 1500 D | 0.9 | 0.1 | 10 | 1200 D |

TABLE 1-continued

| Sample | Solvent | Concentration of init. PA | Amount of H2O2 30% | Temperature (° C.) | Duration | MM Init. PA | q require. free | z oxyd. | n | MM final product |
|---|---|---|---|---|---|---|---|---|---|---|
| CPNO-1-3 | 96% ethyl alcohol | 10 g in 300 ml | 30 ml | 4 | 20 h | 100000 D | 0.2 | 0.8 | 800 | 100000 D |
| CPNO-2-1 | 0.1N . . . | 10 g in 150 ml | ml | 4 | 24 h | 75000 D | 0.2 | 0.8 | 650 | 80000 D |
| CPNO-2-2 | 0.1N . . . | 10 g in 300 ml | ml | 4 | 20 h | 10000 D | 0.6 | 0.4 | 600 | 70000 D |
| CPNO-2-3 | 0.1N . . . | 10 g in 200 ml | ml | 4 | 25 h | 50000 D | 0.5 | 0.5 | 850 | 40000 D |
| CPNO-3-1 | 0.1N . . . | 10 g in 400 ml | ml | 4-6 | 35 h | 80000 D | 0.25 | 0.75 | 700 | 85000 D |
| CPNO-3-2 | 0.1N . . . | 10 g in 150 ml | ml | 4-6 | 45 h | 30000 D | 0.1 | 0.9 | 200 | 22000 D |
| CPNO-3-3 | 0.1N . . . | 10 g in 200 ml | ml | 4 | 25 h | 15000 D | 0.5 | 0.5 | 900 | 110000 D |

TABLE 2

Pharmacokinetic parameters of CP-NO

| Pharmacokinetic parameters | Designation | Measurement units | CP-NO 3-1 | CP-NO 2-1 | CP-NO 1-1 |
|---|---|---|---|---|---|
| Maximum concentration in blood plasma | $C_{max}$ | µg/ml | 17.5 ± 0.20 | 21.4 ± 0.6 | 19.8 ± 0.3 |
| Time of reaching the maximum concentration in blood plasma | $T_{max}$ | Hour | 0.65 ± 0.1 | 0.83 ± 0.15 | 0.43 ± 0.1 |
| Distribution half-life Rapid α-phase | $T_{1/2}\alpha$ | Hour | 0.44 ± 0.06 | 0.56 ± 0.07 | 0.31 ± 0.05 |
| Distribution half-life Slow β-phase | $T_{1/2}\beta$ | Hour | 36.2 ± 7.78 | 43.2 ± 8.3 | 24.6 ± 6.17 |
| Mean retention time of preparation in organism | MRT | Hour | 38.7 ± 6.75 | 57 ± 8.5 | 27.1 ± 5.3 |
| Relative bioavailability | f | % | 89.4 ± 5.77 | 81.6 ± 7.2 | 95.4 ± 3.1 |

TABLE 3

Detoxification properties of CO-NO

| Group | Dose (mg/kg) MRM | Dose (mg/kg) CPNO | Administered volume, ml/20 g | Number of mice in a group | Mortality Dead/alive |
|---|---|---|---|---|---|
| Control | — | — | 0.5 | 6 | 0/6 |
| MRM | 10 | — | 0.25 | 6 | 3/3 |
| MRM | 10 | — | 0.5 | 6 | 6/0 |
| MRM + CPNO-3-1 | 10 | 10 | 0.5 | 6 | 2/4 |
| MRM + CPNO-3-2 | 10 | 50 | 0.5 | 6 | 1/5 |
| MRM + CPNO-1-2 | 10 | 30 | 0.5 | 6 | 1/5 |
| MRM + CPNO-2-1 | 10 | 20 | 0.5 | 6 | 2/4 |

TABLE 4

Antidotal properties of CP-NO-3-1 under the influence of lethal doses of copper salts

| Animal groups | Preparation doses (Mg/kg) CuSO4 | Preparation doses (Mg/kg) CPNO-3-1 | % of animal death at days 1-2 | Animal survivability at day 30 (5%) |
|---|---|---|---|---|
| 1 | — | — | 0 | 0 |
| 2 | 12.5 | — | 100 | 0 |
| 3 | 25.0 | — | 100 | 0 |
| 4 | 50.0 | — | 100 | 0 |
| 5 | 12.5 | 12.5 | 0 | 100 |
| 6 | 25.0 | 25.0 | 0 | 100 |
| 7 | 50.0 | 50.0 | 0 | 100 |

TABLE 5

Detoxificaton and membrane-stabilizing properties of CO-NO (on an erythrocyte hemolysis model under effect of silicon dioxide)

| NoNo of groups | Investigated compound Preparation name | Dose µg/ml | Hemolysis, % | Protection from hemolysis |
|---|---|---|---|---|
| 1 | Henx solution | 3 ml | 100.0 | 0 |
| 2 | CPNO-3-2 | 5 | 33.3* | 66.7* |
| 3 |  | 10 | 19.7* | 80.3* |
| 4 |  | 50 | 5.4* | 94.6* |
| 5 | Hemodez | 1000 | 66.6 | 33.4 |
| 6 |  | 15000 | 17.9* | 82.1* |
| 7 | Polyglucin | 15000 | 82.8 | 17.2 |
| 8 | Albumin | 100 | 82.0 | 18.0 |
| 9 |  | 1000 | 13.5* | 86.5* |

*statistically valid differences with group 1 at $p < 0.01$ are indicated

TABLE 6

Immunostimulating activity of CP-NO

| Preparation | Preparation parameters | Preparation dose, mg/mouse | Stimulation ratio | Administration method |
|---|---|---|---|---|
| CP-NO-1-1 | n = 626, q = 0.35n, z = 0.65n | 100.0 | 6.2 | Subcutaneously (s/c) |
| CP-NO-1-2 | n = 10, q = 0.9n, z = 0.1n | 1000.0 | 3.2 | Intraperitoneally (i/p) |
| CP-NO-1-3 | n = 800, q = 0.2n, z = 0.8n | 1.0 | 6.3 | s/c |
| CP-NO-2-1 | n = 650 q = 0.2n, z = 0.8n | 10.0 | 6.1 | s/c |
| CP-NO-2-2 | n = 600, q = 0.6n, z = 0.4n | 500.0 | 4.4 | i/p |

TABLE 6-continued

Immunostimulating activity of CP-NO

| Preparation | Preparation parameters | Preparation dose, mg/mouse | Stimulation ratio | Administration method |
|---|---|---|---|---|
| CP-NO-2-3 | $n = 850$, $q = 0.5n$, $z = 0.5n$ | 200.0 | 5.3 | s/c |
| CP-NO-3-1 | $n = 700$, $q = 0.25n$, $z = 0.75n$ | 50.0 | 6.5 | s/c |
| CP-NO-3-2 | $n = 200$, $q = 0.1n$, $z = 0.9n$ | 100.0 | 3.8 | i/p |
| CP-NO-3-3 | $n = 900$, $q = 0.5n$, $z = 0.5n$ | 20.0 | 6.8 | s/c |

TABLE 7

Characteristics of the resultant variants of anti-tuberculosis vaccine

| Series | AC dose, μg/mouse | Protein dose, μg/mouse | CP-NO dose, μg/mouse | Ratio AC/CP-NO | Ratio protein/CP-NO |
|---|---|---|---|---|---|
| Preparation 1 | 100 | 5.0 | 500 | 1:5 | 1:100 |
| Preparation 1 | 50 | 2.5 | 500 | 1:10 | 1:200 |

TABLE 8

Isolation rate of mycobacteria from lungs and spleen of inoculated mice after administration of the preparation

| Group No | Group designation | CFU number in lungs | CFU number in spleen |
|---|---|---|---|
| 1 | Preparation 1 | $(3.2 \pm 0.7) \times 10^7$ | $(3.2 \pm 0.7) \times 10^6$ |
| 2 | Preparation 2 | $(4.2 \pm 1.2) \times 10^7$ | $(2.6 \pm 0.5) \times 10^6$ |
| 3 | Preparation 3 | $(6.2 \pm 0.4) \times 10^7$ | $(5.2 \pm 1.1) \times 10^6$ |
| 4 | Control | $(5.6 \pm 1.6) \times 10^7$ | $(8.1 \pm 2.6) \times 10^6$ |

TABLE 9

Survivability of vaccinated animals

| Group No | Number of animals in group | Group designation | Average life time (days) |
|---|---|---|---|
| 1 | 9 | Preparation 1 | $44 \pm 4.8$ |
| 2 | 7 | Preparation 2 | >64 |
| 3 | 9 | Preparation 3 | $32 \pm 5.3$ |
| 4 | 11 | BCG (Praque) $10^6$ | $53 \pm 7.7$ |
| 5 | 9 | Control | $28 \pm 1.6$ |

TABLE 10

Protective properties of conjugate series of Vi-antigen with CP-NO

| Preparation | Immunization dose, μg Vi-PS/mouse | Inoculation dose (TS No 4446) after a month | Percentage of survived animals |
|---|---|---|---|
| Sample 1 | 5 | 1.2 | 100 |
|  |  | 3.6 | 100 |
|  |  | 10.8 | 100 |
| Sample 2 | 5 | 1.2 | 100 |
|  |  | 3.6 | 100 |
|  |  | 10.8 | 25 |
| Vi-PS | 5 | 1.2 | 40 |
|  |  | 3.6 | 25 |
|  |  | 10.8 | 0 |
| Commercial vaccine | 5 | 1.2 | 100 |
|  |  | 3.6 | 40 |
|  |  | 10.8 | 0 |

TABLE 11

Temperature response in rabbits after administration of the commercial vaccine and vaccine of Vi-PS with CP-NO

| NN of rabbits | Prepa-ration | Dose, μg | initial | 1 hour | 2 hours | 3 hours | days |
|---|---|---|---|---|---|---|---|
| 1. | Sample N1 | 1000 | 39.4 | 39.1 | 39.25 | 39.45 | 39.1 |
| 2. |  | 1000 | 38.8 | 39.1 | 39.7 | 39.55 | 38.9 |
| 3. |  | 1000 | 38.6 | 39.6 | 39.45 | 39.55 | 38.6 |
| 4. | Sample 2 | 200 | 38.85 | 38.6 | 38.7 | 39.05 | 38.7 |
| 5. |  | 200 | 39.05 | 39.0 | 38.9 | 39.0 | 38.6 |
| 6. |  | 200 | 38.4 | 38.8 | 38.95 | 38.3 | 38.4 |
| 7. | Vaccine chemical sorbed | 40 | 39.1 | 40.55 | 39.7 | 39.95 | 38.1 |
| 8. |  | 40 | 39.0 | 39.8 | 39.75 | 39.2 | 39.8 |
| 9. |  | 40 | 38.2 | 40.1 | 39.4 | 39.25 | 39.1 |

TABLE 12

Antibody titers induced by variants of candidate vaccine

| | PG-1 | | PG-2 | | PG-3 | | PG-4 | | PG-1 | |
|---|---|---|---|---|---|---|---|---|---|---|
| | OD | OD/ODcrit | OD/ | OD/ODcrit | OD | OD/ODcrit | OD | OD/ODcrit | OD | OD/ODcrit |
| After the first immunization | | | | | | | | | | |
| Av. value | 1.1 | 7.8 | 0.7 | 4.5 | 1.0 | 7.2 | 1.1 | 7.7 | 0.9 | 6.5 |
| Dev. | 0.90 | 6.1 | 0.2 | 1.2 | 0.8 | 5.4 | 1.0 | 6.7 | 0.3 | 2.0 |
| After the second immunization | | | | | | | | | | |
| Av. value | 2.4 | 16.6 | 2.7 | 18.9 | 2.7 | 18.6 | 2.4 | 16.4 | 2.8 | 19.1 |
| Dev. | 0.6 | 4.0 | 0.3 | 2.2 | 0.4 | 2.4 | 0.3 | 2.2 | 0.3 | 1.8 |

TABLE 12-continued

Antibody titers induced by variants of candidate vaccine

| | Group | | | | | | | | |
|---|---|---|---|---|---|---|---|---|---|
| | PG-1 | | PG-2 | | PG-3 | | PG-4 | | PG-1 |
| | OD | OD/ODcrit | OD/ | OD/ODcrit | OD | OD/ODcrit | OD | OD/ODcrit | OD OD/ODcrit |

After the third immunization

| | | | | | | | | | |
|---|---|---|---|---|---|---|---|---|---|
| Av. value | 3.0 | 20.6 | 2.9 | 19.8 | 2.8 | 19.6 | 3.0 | 20.7 | 2.6 17.7 |
| Dev. | 0.0 | 0.3 | 0.2 | 1.2 | 0.3 | 2.0 | 0.0 | 0.0 | 0.5 3.4 |

TABLE 13

Producing antibodies by different line mice in 2 weeks after reimmunization with preparations containing influenza virus hemagglutinin (antibody titer in EIA)

| | Average antibody titer to hemmagglutinin after mouse immunization | | |
|---|---|---|---|
| Mouse line | Hemagglutinin (HA) | Complex of HA with immunoadjuvant CP-NO | Conjugate of HA with immunoadjuvant CP-NO |
| CC57W | 57 052 | 99 334 | 2 408 995 |
| B10CW | 489 178 | 561 918 | 2 767 209 |
| CBA | 57052 | 262 144 | 1 290 948 |
| A/Sn | 161396 | 741455 | 3 913 424 |

The invention claimed is:

1. A heterochain aliphatic poly-N-oxide copolymer of formula (2)

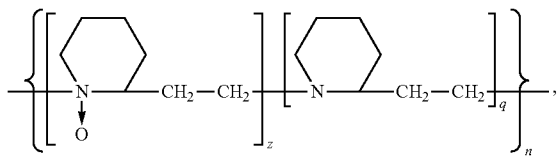

where $z=(0.1\text{-}0.9)_n$,
$q=(0.1\text{-}0.9)_n$, and
$n=10\text{-}1000$, and formula (2)
is a conidine and conidine-N-oxide copolymer.

2. A heterochain aliphatic poly-N-oxide copolymer of formula (3)

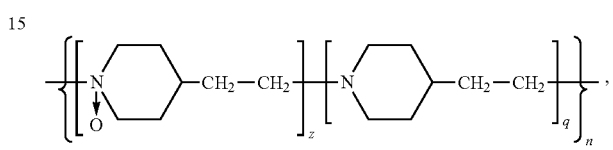

where $z=(0.1\text{-}0.9)_n$,
$q=(0.1\text{-}0.9)_n$, and
$n=10\text{-}1000$, and formula (3)
is a quinuclidine and quinuclidine N-oxide copolymer.

3. A vaccine against hepatitis "A" and hepatitis "B", characterized in that it comprises a vaccine preparation having simultaneously HVA Ag and HBsAg and a heterochain aliphatic poly-N-oxide copolymer of formula (1):

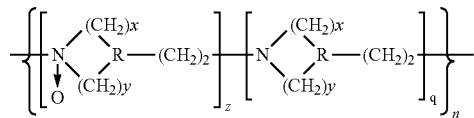

where R=N or CH;
$x=2$ or 4; $y=0$ or 2; $n=10\text{-}1000$; $q=(0.1\text{-}0.9)_n$; $z=(0.1\text{-}0.9)_n$,
wherein HVA Ag antigens are derived from strain LBA-86 of hepatitis A virus in a culture of continuous cells 4647, and the content of components in a dose is
HVA Ag 40-60 EIA u.
HBsAg 2.5-20 μg and
CP—NO 0.1-10 mg.

* * * * *